(12) United States Patent
Fagan et al.

(10) Patent No.: US 11,766,275 B2
(45) Date of Patent: Sep. 26, 2023

(54) ARTICULATING ULTRASONIC SURGICAL INSTRUMENTS AND SYSTEMS

(71) Applicant: Covidien LP, Mansfield, MA (US)

(72) Inventors: James R. Fagan, Erie, CO (US); Thomas E. Drochner, Longmont, CO (US); Michael B. Lyons, Boulder, CO (US); David J. Van Tol, Boulder, CO (US); Matthew S. Cowley, Fredrick, CO (US)

(73) Assignee: Covidien LP, Mansfield, MA (US)

( * ) Notice: Subject to any disclaimer, the term of this patent is extended or adjusted under 35 U.S.C. 154(b) by 222 days.

(21) Appl. No.: 17/320,321

(22) Filed: May 14, 2021

(65) Prior Publication Data

US 2021/0353324 A1 Nov. 18, 2021

Related U.S. Application Data

(60) Provisional application No. 63/026,323, filed on May 18, 2020, provisional application No. 63/026,377, filed on May 18, 2020.

(51) Int. Cl.
*A61B 17/32* (2006.01)
*A61B 17/00* (2006.01)
(Continued)

(52) U.S. Cl.
CPC ........... *A61B 17/320068* (2013.01); *A61B 17/320092* (2013.01); *A61B 2017/003* (2013.01);
(Continued)

(58) Field of Classification Search
CPC .... A61B 17/320068; A61B 17/320092; A61B 17/320094; A61B 2017/320071;
(Continued)

(56) References Cited

U.S. PATENT DOCUMENTS 5,897,523 A 4/1999 Wright et al.
6,051,010 A 4/2000 DiMatteo et al.
(Continued)

FOREIGN PATENT DOCUMENTS

WO WO-2019018289 A1 * 1/2019 ....... A61B 17/00234

OTHER PUBLICATIONS

Extended European Search Report dated Sep. 30, 2021 issued in corresponding EP Appln. No. 21174172.3.

*Primary Examiner* — Timothy J Neal
*Assistant Examiner* — Mitchell Brian Hoag
(74) *Attorney, Agent, or Firm* — Carter, DeLuca & Farrell LLP

(57) ABSTRACT

A surgical instrument includes a housing having an elongated body extending distally therefrom. The elongated body defines a first articulating portion and a second articulating portion. The elongated body defines a lumen therein. An end effector is supported at a distal end portion of the elongated body. A flexible waveguide extends through the lumen of the elongated body. A proximal end portion of the flexible waveguide connects to an ultrasonic transducer. A distal end portion of the flexible waveguide is connected with the end effector. the flexible waveguide defines a first articulating portion having a narrower thickness than a thickness of other portions of the flexible waveguide and a second articulating portion having a narrower thickness than a thickness of other portions of the flexible waveguide.

25 Claims, 15 Drawing Sheets

(51) Int. Cl.
  *A61B 17/22* (2006.01)
  *A61B 17/29* (2006.01)
(52) U.S. Cl.
  CPC ............... *A61B 2017/00389* (2013.01); *A61B 2017/22018* (2013.01); *A61B 2017/2908* (2013.01); *A61B 2017/2929* (2013.01); *A61B 2017/320071* (2017.08); *A61B 2017/320074* (2017.08)
(58) Field of Classification Search
  CPC .. A61B 2017/2908; A61B 2017/22018; A61B 2017/2929; A61B 2017/003
  See application file for complete search history.

(56) References Cited

U.S. PATENT DOCUMENTS

| | | | |
|---|---|---|---|
| 6,063,098 | A | 5/2000 | Houser et al. |
| 6,589,200 | B1 | 7/2003 | Schwemberger et al. |
| 6,752,815 | B2 | 6/2004 | Beaupre |
| 6,783,524 | B2 | 8/2004 | Anderson et al. |
| 7,135,030 | B2 | 11/2006 | Schwemberger et al. |
| 7,837,699 | B2 | 11/2010 | Yamada et al. |
| 7,922,651 | B2 | 4/2011 | Yamada et al. |
| 9,095,367 | B2 | 8/2015 | Olson et al. |
| 9,314,308 | B2 | 4/2016 | Parihar et al. |
| 9,393,037 | B2 | 7/2016 | Olson et al. |
| 9,408,622 | B2 | 8/2016 | Stulen |
| 9,655,614 | B2 | 5/2017 | Swensgard et al. |
| 10,029,125 | B2 | 7/2018 | Shapiro et al. |
| 10,034,683 | B2 | 7/2018 | Monroe et al. |
| 10,172,636 | B2 | 1/2019 | Stulen et al. |
| 10,226,274 | B2 | 3/2019 | Worrell et al. |
| 10,258,363 | B2 | 4/2019 | Worrell et al. |
| 10,413,316 | B2 | 9/2019 | Lyons |
| 2002/0128674 | A1* | 9/2002 | Beaupre .................. B06B 3/00 606/169 |
| 2006/0058825 | A1 | 3/2006 | Ogura et al. |
| 2012/0078248 | A1* | 3/2012 | Worrell ............. A61B 18/1447 606/45 |
| 2014/0005701 | A1 | 1/2014 | Olson et al. |
| 2014/0005702 | A1* | 1/2014 | Timm .................... A61B 17/29 606/169 |
| 2014/0114334 | A1* | 4/2014 | Olson .................... A61B 34/37 606/169 |
| 2014/0276931 | A1 | 9/2014 | Parihar et al. |
| 2014/0309562 | A1 | 10/2014 | Ito |
| 2014/0350570 | A1 | 11/2014 | Lee |
| 2015/0066022 | A1* | 3/2015 | Shelton, IV ....... A61B 18/1445 606/41 |
| 2015/0066067 | A1* | 3/2015 | Stulen ............. A61B 17/320092 53/428 |
| 2015/0080924 | A1 | 3/2015 | Stulen et al. |
| 2015/0157355 | A1* | 6/2015 | Price ............. A61B 17/320068 606/169 |
| 2015/0320438 | A1 | 11/2015 | Weisenburgh, II et al. |
| 2016/0302812 | A1 | 10/2016 | Monroe et al. |
| 2016/0302818 | A1 | 10/2016 | Weisenburgh, II et al. |
| 2016/0302819 | A1 | 10/2016 | Stulen et al. |
| 2017/0135718 | A1 | 5/2017 | Lyons |
| 2017/0245875 | A1 | 8/2017 | Timm et al. |
| 2017/0281218 | A1 | 10/2017 | Timm |
| 2017/0281220 | A1 | 10/2017 | Hibner et al. |
| 2018/0168681 | A1 | 6/2018 | Kirk et al. |
| 2019/0021752 | A1 | 1/2019 | Boudreaux |
| 2019/0021756 | A1* | 1/2019 | Boudreaux ...... A61B 17/00234 |
| 2019/0029712 | A1 | 1/2019 | Stoddard et al. |
| 2020/0008827 | A1* | 1/2020 | Dearden ............. B25J 15/0233 |
| 2021/0059710 | A1* | 3/2021 | Black ................. A61B 17/295 |
| 2021/0059711 | A1* | 3/2021 | Hunter .......... A61B 17/320068 |

* cited by examiner

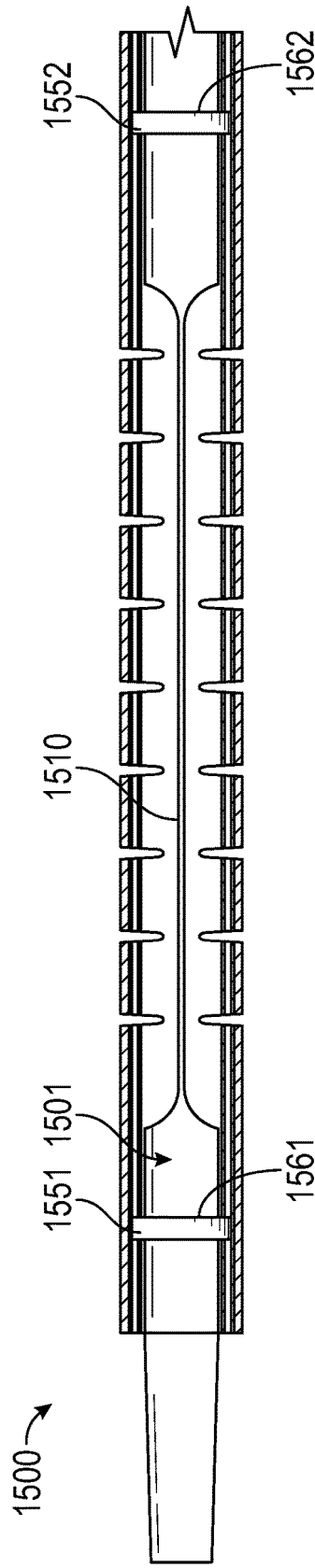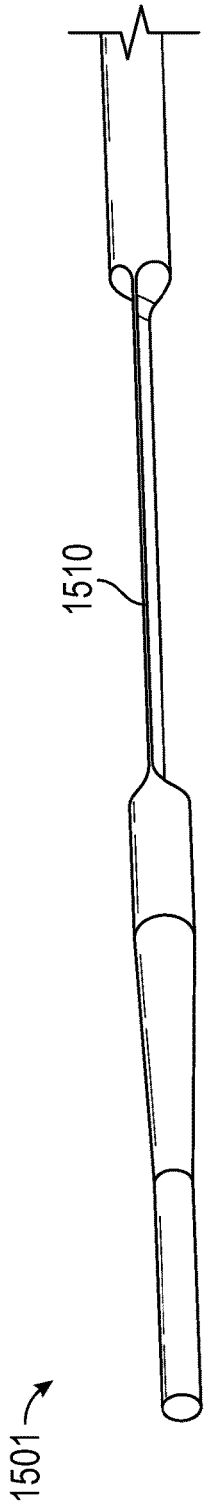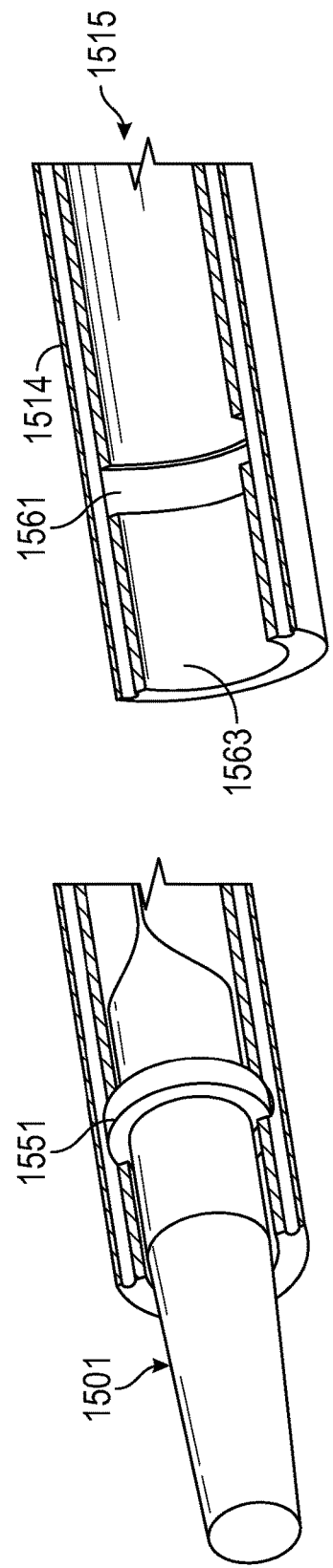
FIG. 15A
FIG. 15B
FIG. 15C
FIG. 15D

ARTICULATING ULTRASONIC SURGICAL INSTRUMENTS AND SYSTEMS

CROSS-REFERENCE TO RELATED APPLICATIONS

The present application claims the benefit of and priority to U.S. Provisional Patent Applications Nos. 63/026,323 and 63/026,377, each of which was filed on May 18, 2020. The entire contents of each of the foregoing applications are incorporated by reference herein.

FIELD

The present disclosure relates to surgical instruments and systems and, more particularly, to articulating ultrasonic surgical instruments and systems.

BACKGROUND

Ultrasonic surgical instruments and systems utilize ultrasonic energy, i.e., ultrasonic vibrations, to treat tissue. More specifically, a typical ultrasonic surgical instrument or system includes a transducer configured to produce and transmit mechanical vibration energy at ultrasonic frequencies along a waveguide to an ultrasonic end effector configured to treat tissue, e.g., coagulate, cauterize, fuse, seal, cut, desiccate, fulgurate, or otherwise treat tissue. Traditionally, the transducer remains external of the surgical site, while the waveguide extends from the transducer into the surgical site to provide the ultrasonic energy to the ultrasonic end effector. The ultrasonic end effector is manipulated into position to treat a desired tissue or tissues.

Some ultrasonic surgical instruments and systems incorporate rotation features, thus enabling rotation of the ultrasonic end effector to a desired orientation within the surgical site. However, even in such instruments and systems, the ability to navigate within the surgical site via rotation and manipulation alone is limited.

SUMMARY

In one aspect of the disclosure, a surgical instrument includes a housing having an elongated body extending distally therefrom. The elongated body defines a first articulating portion and a second articulating portion. The elongated body defines a lumen therein. An end effector is supported at a distal end portion of the elongated body. A flexible waveguide extends through the lumen of the elongated body. A proximal end portion of the flexible waveguide connects to an ultrasonic transducer. A distal end portion of the flexible waveguide is connected with the end effector. The flexible waveguide defines a first articulating portion having a narrower thickness than a thickness of other portions of the flexible waveguide and a second articulating portion having a narrower thickness than a thickness of other portions of the flexible waveguide.

In some aspects of the disclosure, the first articulating portion of the flexible waveguide is configured to articulate in a first orientation, and the second articulating portion of the flexible waveguide is configured to articulate in a second orientation. The first articulating portion of the flexible waveguide and the second articulating portion of the flexible waveguide may each articulate in a same orientation as each other, or different orientations from each other. The first or second articulating portions of the flexible waveguide is configured to articulate from about 1 degree to about 45 degrees.

In some aspects of the disclosure, the end effector includes an ultrasonic blade and a jaw configured to rotate about the ultrasonic blade. The ultrasonic blade and the jaw are configured to capture and treat tissue therebetween in plural rotational orientations of the jaw relative to the ultrasonic blade.

In some aspects of the disclosure, the elongated body is configured to rotate to achieve different directional orientations of the end effector. Independent controls are configured to rotate the elongated body, rotate the jaw about the ultrasonic blade, and articulate the first articulating portion and the second articulating portion of the elongated body. Thus, the first articulating portion of the flexible waveguide and the second articulating portion of the flexible waveguide are correspondingly rotated by the independent controls.

In some aspects of the disclosure, first and second transducers are at opposite sides of the first articulating portion of the flexible waveguide. At least one of the first or second transducers is configured to amplify an ultrasonic wave transmitted through the first articulating portion of the flexible waveguide.

In some aspects of the disclosure, the flexible waveguide may define a single articulating portion having a narrower width than a width of other portions of the flexible waveguide, and the elongated body may be configured to rotate to achieve different directional orientations of the end effector.

Other features of the disclosure will be appreciated from the following description.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which:

FIG. 15A is a longitudinal, cross-sectional view of a flexible waveguide secured within a lumen of an elongated body by a removable annular collar;

FIG. 15B is a perspective view of the flexible waveguide of FIG. 15A with the removable annular collar omitted;

FIG. 15C is a longitudinal, cross-sectional view of the removable annular collar positioned about the flexible waveguide and secured in the lumen by a recess formed in an inner surface of the elongated body of FIG. 15A; and FIG. 15D is a longitudinal, cross-sectional view of the recess of FIG. 15C.

DETAILED DESCRIPTION

Figure 1:
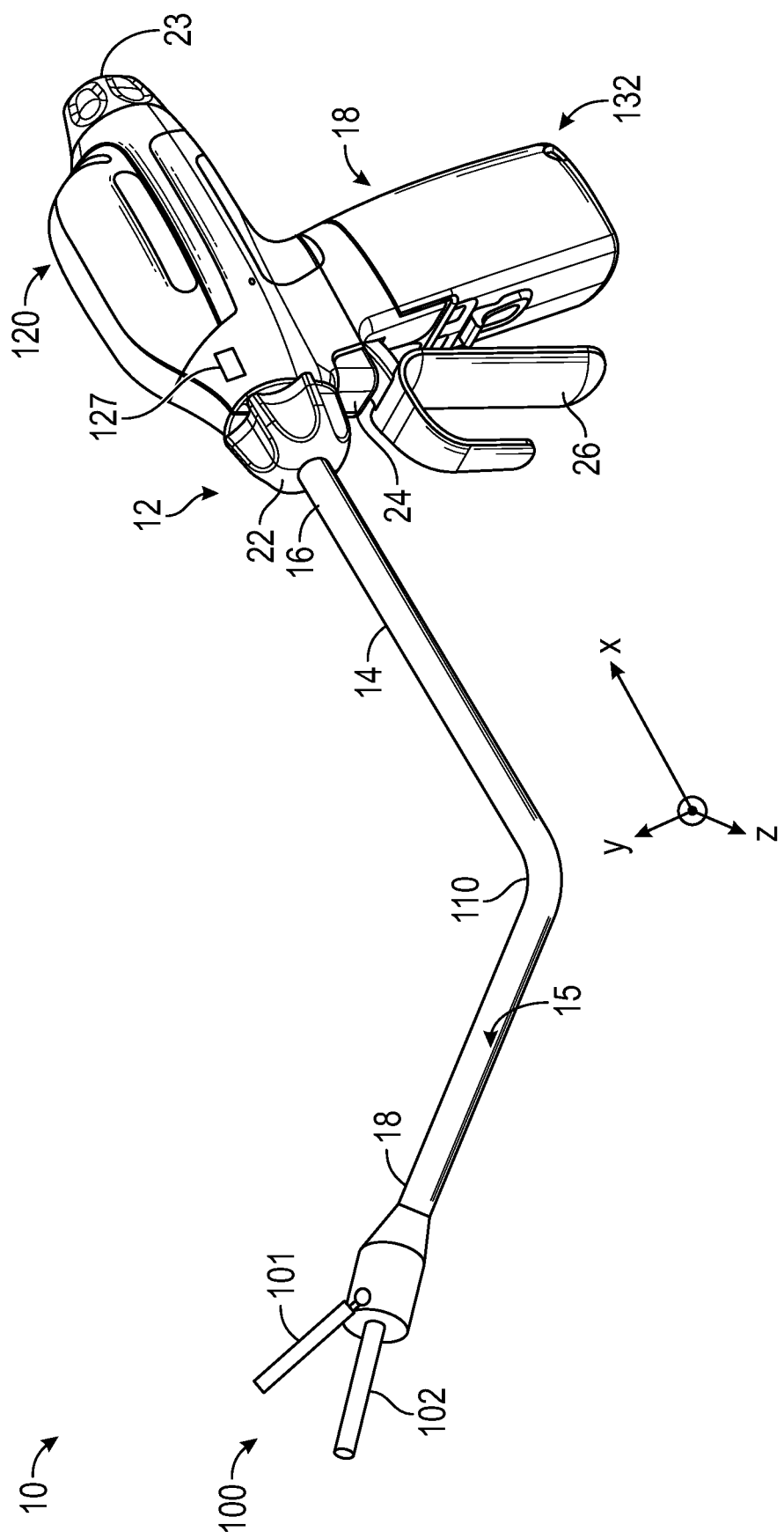
FIG. 1 is a side, perspective view of a surgical instrument having an articulating portion configured for use in accordance with the aspects and features of present disclosure.
Figure 2:
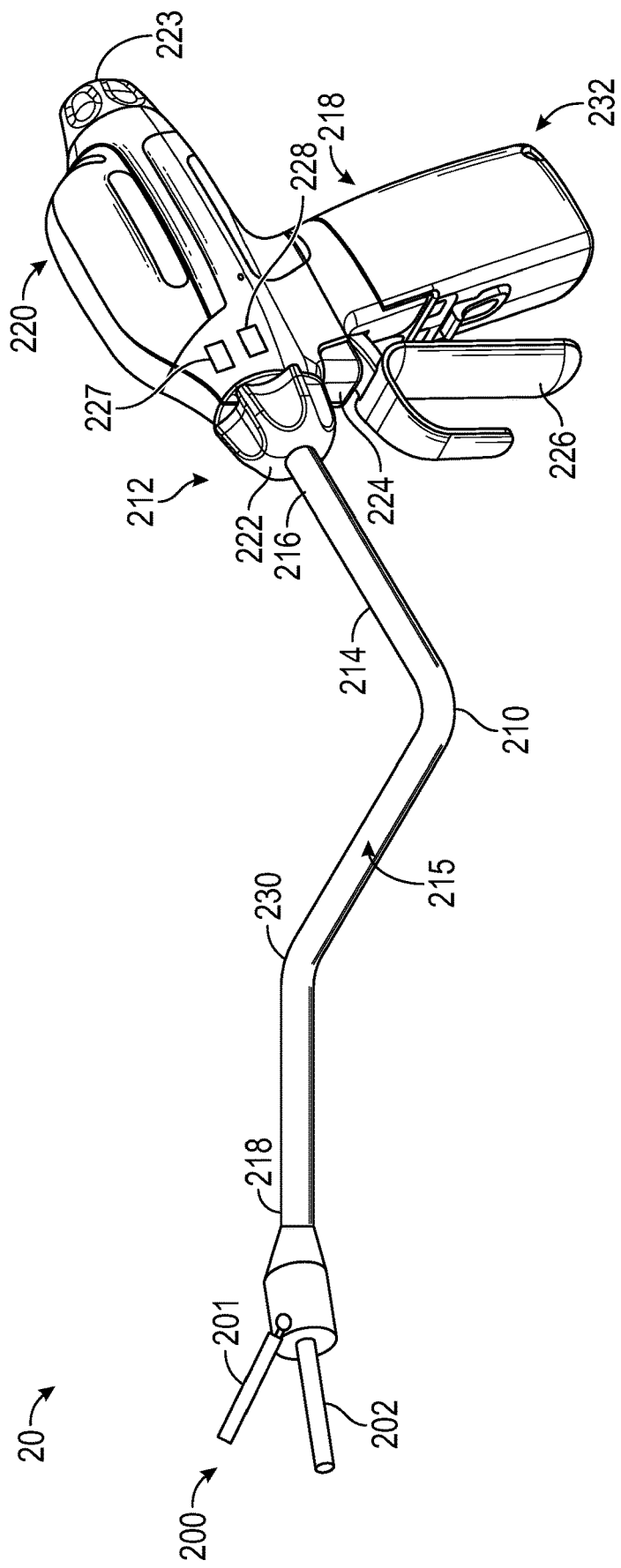
FIG. 2 is a side, perspective view of a surgical instrument having first and second articulating portions configured for use in accordance with the aspects and features of present disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

Exemplary axes or directions such as an X-axis direction, a Y-axis direction and a Z-axis direction may be illustrated in the accompanying drawings and/or described herein. As an example, the X-axis direction may perpendicular to the Y-axis direction, and the Z-axis direction may be orthogonal to the X-axis direction and the Y-axis direction.

"About" or "approximately" or "substantially" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Exemplary embodiments of the disclosure will be described more fully below (e.g., with reference to the accompanying drawings). Like reference numerals may refer to like elements throughout the specification and drawings.

Generally, in the flexible waveguide described herein (e.g., flexible waveguides 301, 401, 801, 1001, 1201, 1301, 1401 and 1501), the ultrasonic waveguide is thinned down enough at articulating portions thereof (e.g., articulating portions 310, 410, 430, 810, 1010, 1210, 1310, 1410 and 1510) to be elastically flexible, but still has enough material to carry the ultrasonic wave to the tip of the instrument (e.g. to end effectors 100, 200, and 600 and 700). While the flexible waveguide has a substantially cylindrical shape, the thinned down and elastically flexible sections may be at least partially flattened to create an at least partially flattened cylindrical shape, e.g., including opposed planar surfaces. The term "flattened" relates to the end configuration and not the method of achieving the flexible section(s). The above configuration enables an articulating ultrasonic surgical instrument wherein the ultrasonic transducer would be "outside" the body and the ultrasonic wave would be carried through the flex in the waveguide to the end effector.

End effectors 100, 200, 600 and 700 described herein are substantially the same as each other unless otherwise indicated. Flexible waveguides 301, 401, 801, 1001, 1201, 1301, 1401 and 1501 described herein are substantially the same as each other, unless otherwise indicated. Articulating portions 310, 410, 430, 810, 1010, 1210, 1310, 1410 and 1510 described herein are substantially the same as each other, unless otherwise indicated. Jaw members 101, 201, 601 and 701 described herein are substantially the same as each other, unless otherwise indicated. Blade members 102, 202, 602 and 702 described herein are substantially the same as each other, unless otherwise indicated. Housings 12 and 212 as described herein are substantially the same as each other, unless otherwise indicated. Handle assemblies 132 and 232 described herein are substantially the same as each other, unless otherwise indicated. Stabilizers 351 and 851 described herein are substantially the same as each other, unless otherwise indicated. Stabilizers 352 and 852 described herein are substantially the same as each other, unless otherwise indicated.

Referring generally to FIG. 1, an embodiment of a surgical instrument (e.g., an endoscopic surgical instrument) exemplifying the aspects and features of the present disclosure is shown generally identified by reference numeral 10. For the purposes herein, surgical instrument 10 is generally described. Aspects and features of surgical instrument 10 not germane to the understanding of the present disclosure are omitted to avoid obscuring the aspects and features of the present disclosure in unnecessary detail.

Surgical instrument 10 generally includes a housing 12 (defining a handle assembly 132), an elongated body 14, and an end effector 100. Handle assembly 132 supports a battery assembly 18 and a transducer and generator assembly ("TAG") 120, and includes a first rotation knob 22, a second rotation knob 23, an activation button 24, and a clamp trigger 26.

Elongated body 14 defines a proximal end portion 16 connected with the first rotation knob 22 and a distal end portion 18 supporting end effector 100. End effector 100 includes an ultrasonic blade 102 and a pivoting jaw 101. In embodiments, ultrasonic blade 102 is cylindrical or otherwise includes one or more radial symmetries (or is fully radially symmetric) and jaw 101 is configured to rotate about the ultrasonic blade 102 to enable clamping tissue therebetween at plural (or an infinite number of) orientations. A lumen 15 is defined within elongated body 14.

Clamp trigger 26 of surgical instrument 10 is selectively manipulatable to actuate a motor, other powered drive mechanism, or a manual drive mechanism, e.g., gears, pulleys, tension cables, etc., to pivot jaw 101 relative to ultrasonic blade 102 to thereby transition end effector 100 between an open condition and a clamping condition.

First rotation knob 22 is selectively manipulatable to rotate elongated body 14 and, thus, end effector 100 relative to housing 12. Second rotation knob 23 is selectively manipulatable to actuate a motor, other powered drive mechanism, or a manual drive mechanism, e.g., gears, pulleys, tension cables, etc., to rotate jaw member 101 relative to ultrasonic blade 102. As an alternative to first and second rotation knobs 22, 23, other suitable actuation mechanism, e.g., toggle switches, joysticks, buttons, etc., may be provided. Third rotation knob 127 is selectively manipulatable to articulate articulating portion 110.

Battery assembly 18 and the generator of TAG 120 cooperate, upon activation of activation button 24, to supply power to the transducer of TAG 120 to enable the generation of ultrasonic energy that is transmitted to blade 102 of end effector 100 for treating tissue therewith, e.g., to coagulate, cauterize, fuse, seal, cut, desiccate, fulgurate, or otherwise treat tissue, as detailed below. Battery assembly 18 and TAG 20 are each releasably secured to handle assembly 132, and are removable therefrom to facilitate disposal of handle assembly 132, with the exception of battery assembly 18 and TAG 120. However, it is contemplated that any or all of the components of surgical instrument 10 be configured as disposable single-use components or sterilizable multi-use components, and/or that surgical instrument 10 be connectable to a remote power source or generator rather than having such components on-board.

Referring particularly to FIGS. 1, 3, 6A, 6B, and 7A-7D, surgical instrument 10, as noted above, includes housing 12 and elongated body 14 extending therefrom. Elongated body 14 defines a lumen 15 therein, a proximal end portion 16 and a distal end portion 18 supporting end effector 100. Elongated body 14 includes at least one articulating portion 110 between the proximal end portion 16 and the distal end portion 18. A flexible waveguide (e.g. flexible waveguide 301 of FIG. 3) extends through lumen 15 and includes an articulating portion 310. The articulating portion 110 of elongated body 14 and the articulating portion 310 of flexible waveguide are positioned in substantially a same location along the elongated body 14 such that articulating portion 110 and articulating portion 310 can articulate in a similar manner as each other. Elongated body 14 is configured to rotate in unison with flexible waveguide 310 extending through lumen 15 and jaw member 101 is configured to rotate about blade 102 (see also, e.g., jaw member 601 and blade 602 FIGS. 6A and 6B). Thus, surgical instrument 10 can achieve any desired directional orientation for end effector 100 through a combination of rotating elongated body 14, articulation of articulating portions 110 and 310, and rotating jaw member 101 about blade 102 (see also, e.g., elongated body 714, articulation portion 730, jaw member 701, and blade 702 of FIGS. 7A to 7D). This may be achieved with a single articulating region along elongated body 14, or with multiple articulating regions.

Figure 3:
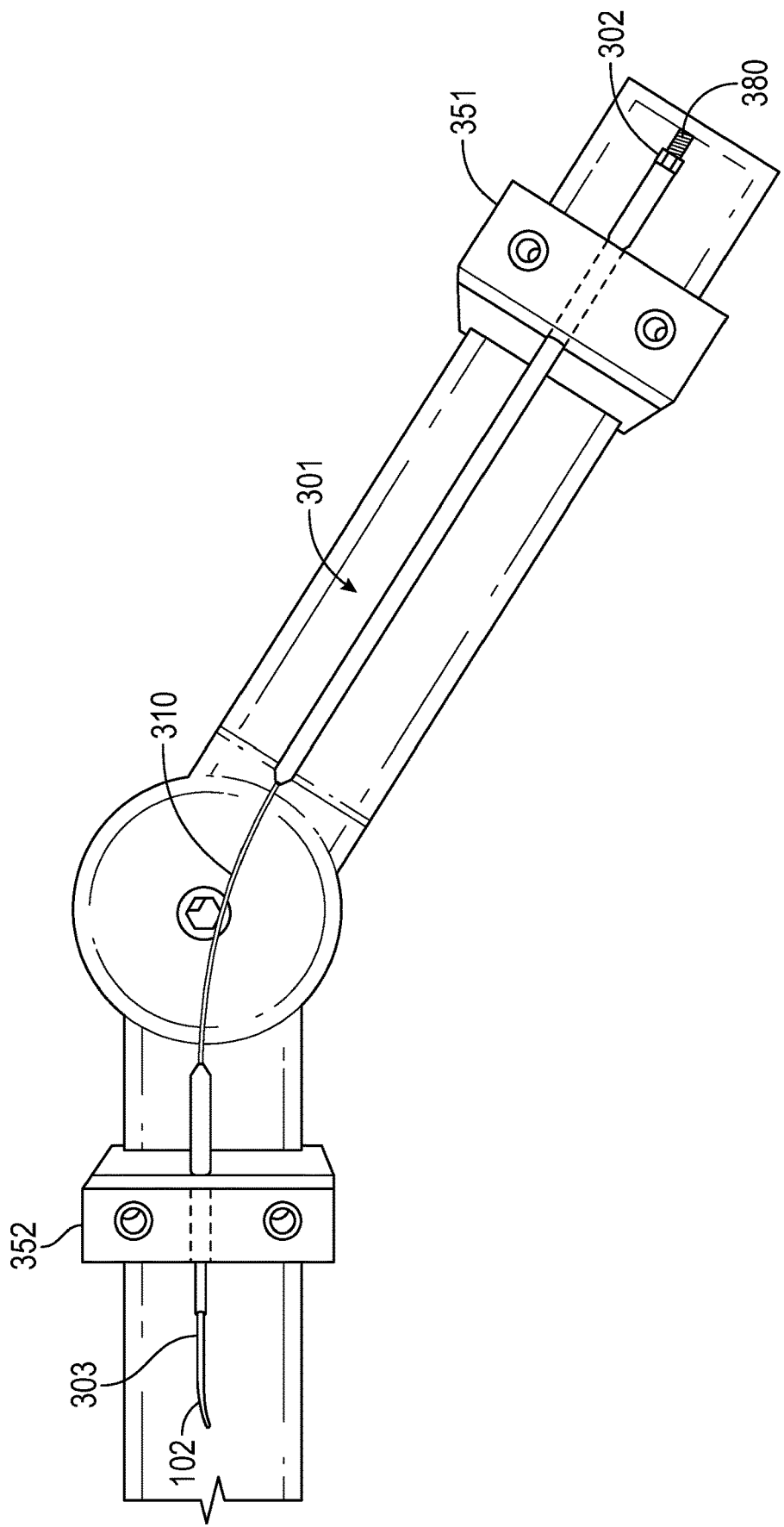
FIG. 3 is a side view of a single conceptualized articulating portion including a flexible waveguide shown restrained in a test fixture representing support, pivot, and other features, the flexible waveguide configured for use with the surgical instrument of FIG. 1.
Figure 4A:
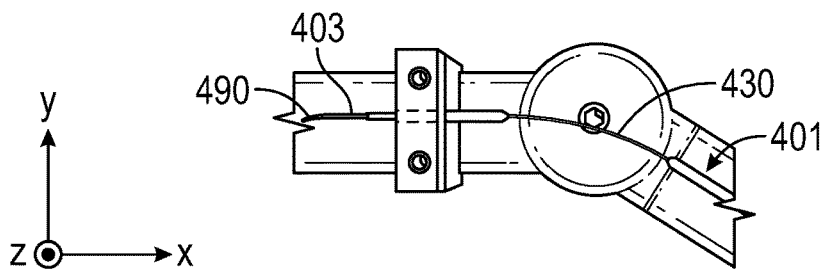
FIG. 4A is a side view of a conceptualized first articulating portion including a first portion of a flexible waveguide shown restrained in a test fixture representing support, pivot, and other features, the flexible waveguide configured for use with the surgical instrument of FIG. 2 articulated in a first plane.
Figure 4B:
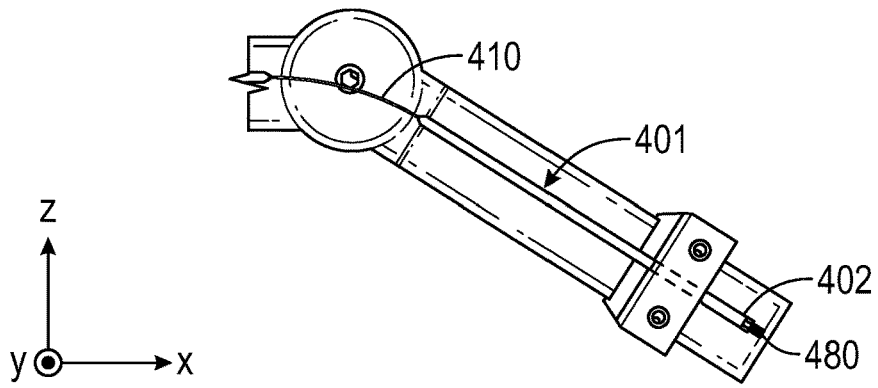
FIG. 4B is a side view of a conceptualized second articulating portion including a second portion of a flexible waveguide shown restrained in a test fixture representing support, pivot, and other features, the flexible waveguide configured for use with the surgical instrument of FIG. 2, articulated in a second plane.

Referring to FIGS. 1 and 3, flexible waveguide 301 extends through the lumen 15 of the elongated body 14. A proximal end portion 302 of the flexible waveguide 301 is connected with the ultrasonic generator 120. A distal end portion 303 of the flexible waveguide 301 is connected, e.g., attached, formed integrally with, etc., to the blade 102 of the end effector 100. The flexible waveguide 301 defines the articulating portion 310 having a narrower dimension, e.g., width, than other portions of the flexible waveguide 301. In this manner, the articulating portion 310 is flexible while the remainder of waveguide 301 is substantially inflexible (e.g., not configured to significantly flex during use). Proximal end portion 302 may define a threaded end 380 for connecting with ultrasonic generator 120 and distal end portion 303 may define blade 102.

The articulating portion including articulation portion 110 of elongated body 14, and articulating portion 310 of waveguide 301 may enable articulation relative to a single plane defined by the thinned portion (articulating portion 310) of the flexible waveguide 301. Blade 102, as noted above, is cylindrical or otherwise defines one or more radial symmetries and rotatable jaw 101 is rotatable about blade 102. The blade 102 may have a curved or partially curved configuration (see, e.g., FIG. 3) or a substantially straight configuration (see, e.g., FIG. 6B). By making the blade 102 cylindrical or otherwise defining one or more radial symmetries, it allows for clamping jaw 101 on the blade 102 at plural points or any point on an outer surface thereof while allowing for achievement of the same tissue effect. The flexible waveguide 301 is substantially cylindrical along a majority of the length thereof, and further includes articulating portion 310 having a flattened cylindrical shape. Because of the cylindrical waveguide, the jaw 101 can rotate around the blade 102, while the blade 102 is stationary.

Referring to FIGS. 2, 4A, 4B, 5A, and 5B, surgical instrument 20 is substantially the same as surgical instrument 10, except for having a first articulating portion 210 and a second articulating portion 230. Each articulating portion 210 and 230 may achieve a somewhat gentle bend (e.g., from about 1 degree to about 45 degrees) about a single, but different plane from each other. Surgical instrument 20 generally includes a housing 212 (defining a handle assembly 232), an elongated body 214 defining a proximal end portion 216 and a distal end portion 218 and a lumen 215 therein, and an end effector 200. End effector 200 includes an ultrasonic blade 202 and a jaw 201 pivotable relative to ultrasonic blade 202 and that may be configured to rotate about the ultrasonic blade 202. Handle assembly 232 supports a battery assembly 218 and a transducer and generator assembly ("TAG") 220, and includes a first rotation knob 222, a second rotation knob 223, an activation button 224, a clamp trigger 226, a third rotation knob 227 and a fourth rotation knob 228.

Flexible waveguide 401 including first articulating portion 410 and second articulating portion 430 extending through lumen 215 of elongated body 214. The first articulating portion 210 of elongated body 214 and the first articulating portion 410 of flexible waveguide 401 are positioned in substantially a same location as each other along the elongated body 214 such that first articulating portion 210 and first articulating portion 410 can articulate in a similar manner as each other. The second articulating portion 230 of elongated body 214 and the second articulating portion 430 of flexible waveguide 401 are positioned in substantially a same location as each other along the elongated body 214 such that second articulating portion 230 and second articulating portion 430 can articulate in a similar manner as each other, e.g., in a second plane different from a plane of articulation of the first portions 210, 410. Alternatively, the second plane may be substantially the same as the first plane (e.g., the first and second planes may each be along the Y-Axis direction of FIGS. 4A, 4B, 5A, and 5B). For example, the first plane may be along the Y-axis direction of FIGS. 4A, 4B, 5A, and 5B and the second plane may be along the Z-axis direction of FIGS. 4A, 4B, 5A, and 5B. Thus, elongated member 214 and the flexible waveguide 401 extending therethrough may articulate about two different directions to achieve a desired directional orientation of end effector 200 and/or to achieve desired placement of various segments of elongated member 214.

Figure 5A:
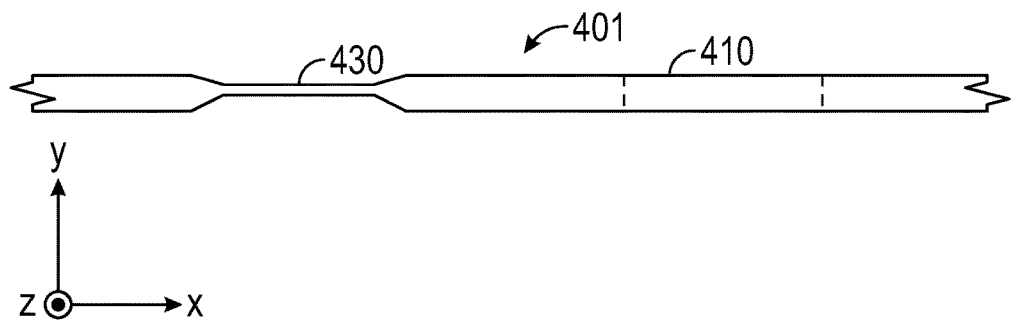
FIG. 5A is a side view of the flexible waveguide of FIG. 4A.
Figure 5B:
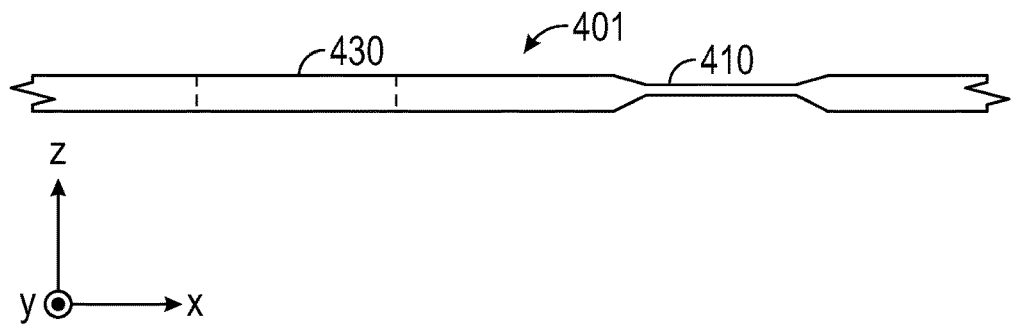
FIG. 5B is a top plan view of the flexible waveguide of FIG. 4A.

Referring particularly to FIGS. 5A and 5B, because the articulating portions 410, 430 of flexible waveguide 401 are formed to have flattened shapes, the thinning of articulation portion 430 of flexible waveguide 401 might only be visible about a single plane (e.g., a side view as in FIG. 5A), while the thinning of articulation portion 410 of flexible waveguide 401 might only be visible about a different single plane (e.g., a plan view as in FIG. 5B).

Figure 8:
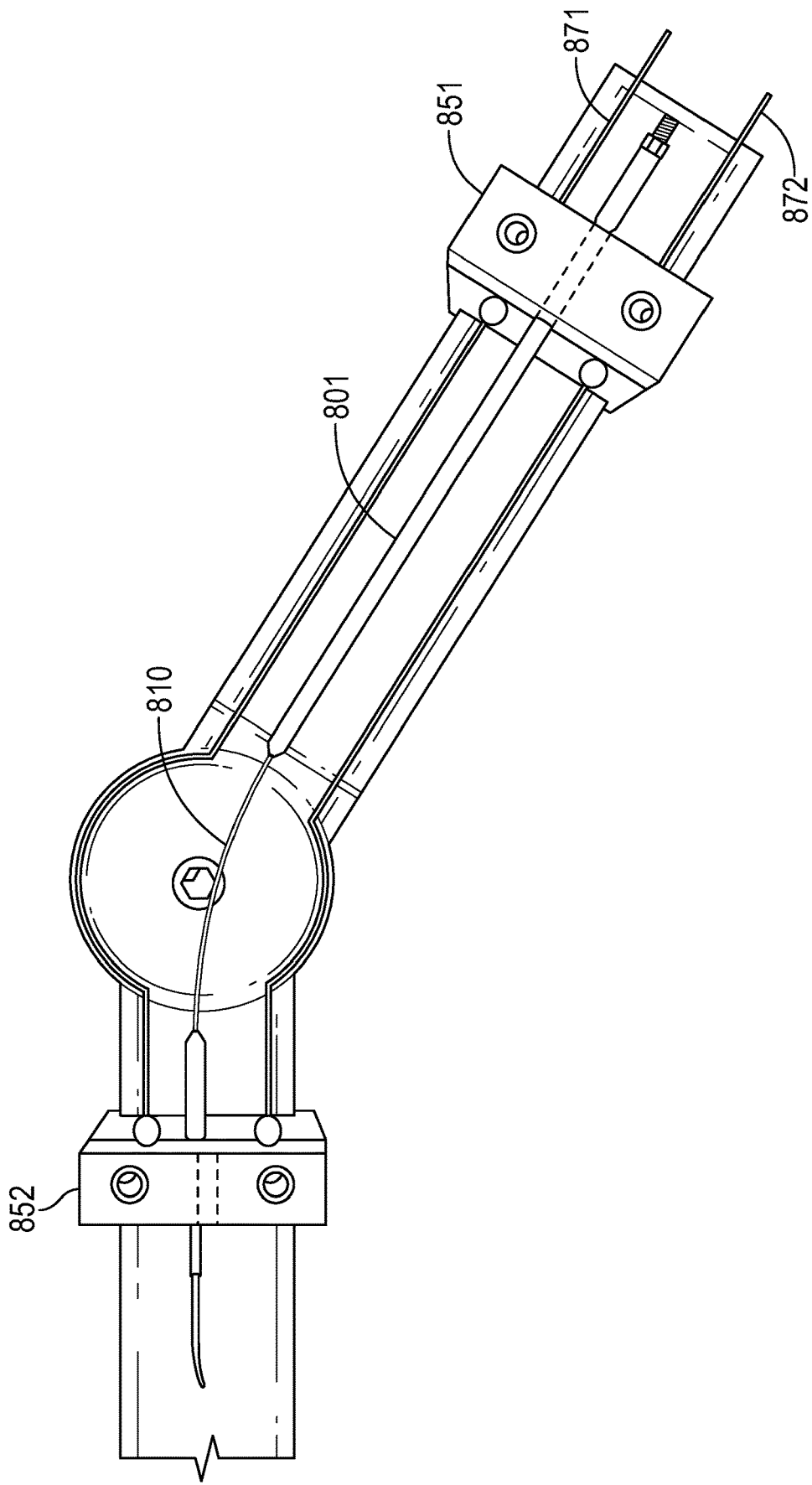
FIG. 8 is a side view of a conceptualized articulation portion including a cable system for articulating the articulating portion and the flexible waveguide, the flexible waveguide shown restrained in a test fixture representing support, pivot, and other features and configured for use with the surgical instrument of FIG. 1 or 2.

Referring particularly to FIG. 8, a cable system including first cable 871 and second cable 872 may be employed for articulating an articulating portion 810 of a flexible waveguide 801. While two cables may be employed, a single cable on a spool may also be employed or more than two cables may be utilized. The cables 871, 872 may route beside the flexible waveguide 801 within a lumen (e.g., lumen 15 or 215 described herein (FIGS. 1 and 2, respectively)). By pulling on one cable 871, 872, and releasing slack in the other cable 871, 872, the articulating portion 810 is urged to articulate in the direction of the tensioned cable. Alternatively, articulating the articulating portion 810 of the flexible waveguide 801 may be achieved by use of a thin wire of nitinol or other material, to push and pull on an inner tube of the elongated portion for flexing actuation. The thin wire may be held in a sleeve or channel to allow for pushing, without buckling. The inner lumen described is employed to house the flexible waveguide 801, while the cable systems and the like described herein employ cables or similar apparatus housed within separate lumens or channels to maintain separation from the flexible waveguide 801.

Referring particularly to FIGS. 3 and 8, stabilizers 351, 851 and 352, 852 may be employed for assisting in the controlled articulation of the flexible waveguide 301, 801. The stabilizers 351, 851 are secured to the flexible waveguide 301, 801 at positions proximal and distal of the articulating portions 310, 810 of the flexible waveguide 301, 801. The stabilizers 351, 851 and 352, 852 may be secured to an inner surface of the elongated member described herein. Thus, proximal/distal movement of the flexible waveguide 301, 801 is inhibited. Holding/stabilizing the flexible waveguide 301, 801 at these locations allows formation of a gradual bend of articulation, without causing a heating/friction point or causing unnecessary noise in the flexible waveguide 301, 801. Although FIGS. 3 and 8 conceptually illustrate elongated bodies including stabilizers 351, 851 holding/stabilizing the flexible waveguides 301, 801, a person of skill in the art would readily appreciate how such stabilizers would, in practice, be incorporated into elongated body 14 (FIG. 1), for holding/stabilizing flexible waveguides 301, 801 therein. Additional stabilizing structures for the flexible waveguide 301, 801 are described below with reference to FIGS. 12A to 15D.

Figure 6B:
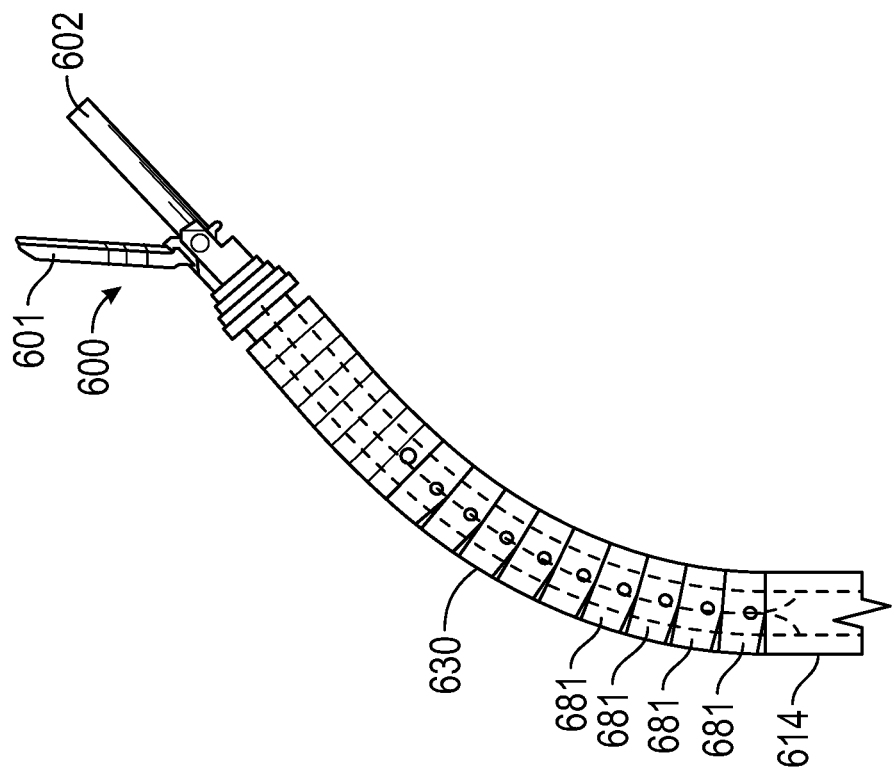
FIG. 6B is a side view of the distal end of the elongated body, and the end effector of FIG. 6A in a second rotational position.
Figure 6A:
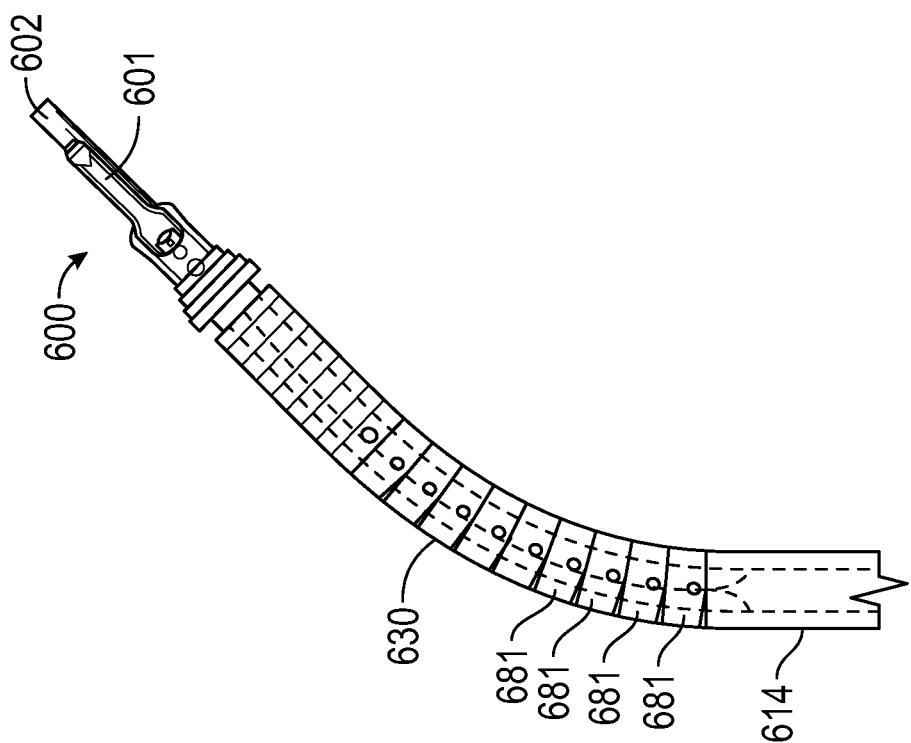
FIG. 6A is a side view of a distal end of an elongated body, and end effector including a rotatable jaw member, configured for use with the surgical instrument of FIG. 1 or 2 in a first rotational position.
Figures 7A, 7B:
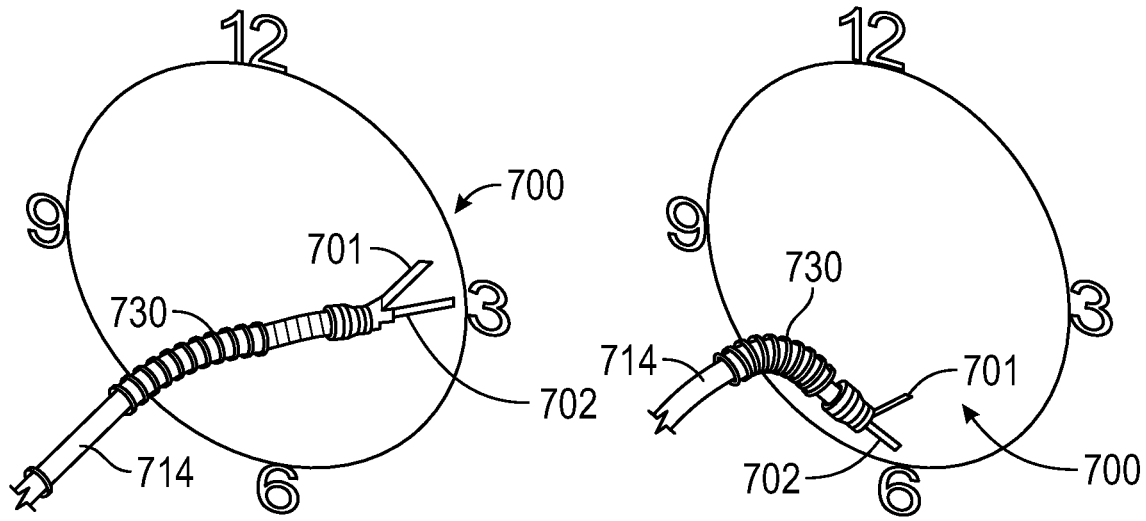
FIGS. 7A-7D are side, perspective views of the elongated body, and end effector including a rotatable jaw member, of FIG. 6A, in various rotational and articulated orientations.
Figures 7C, 7D:
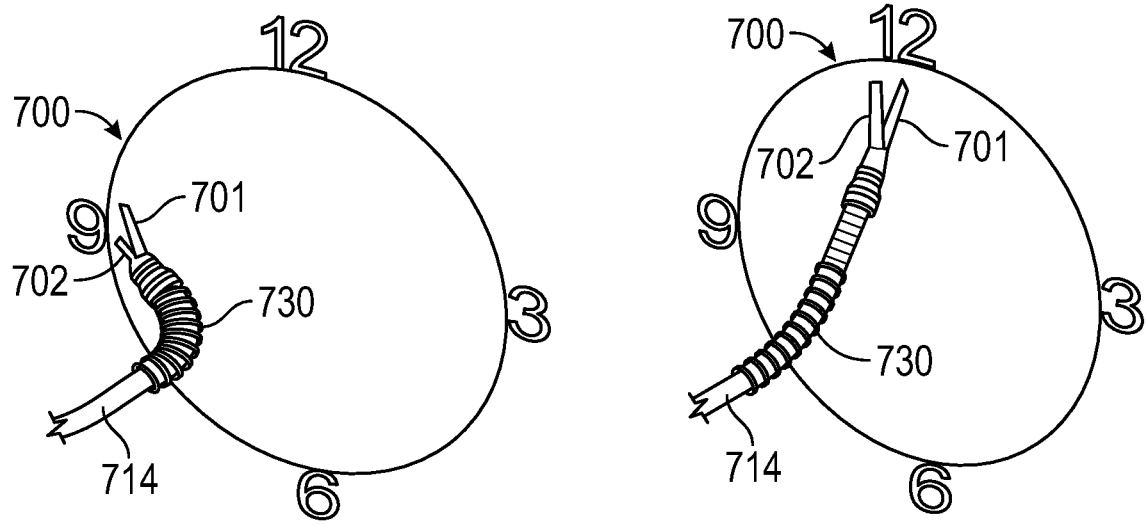
Figure 9:
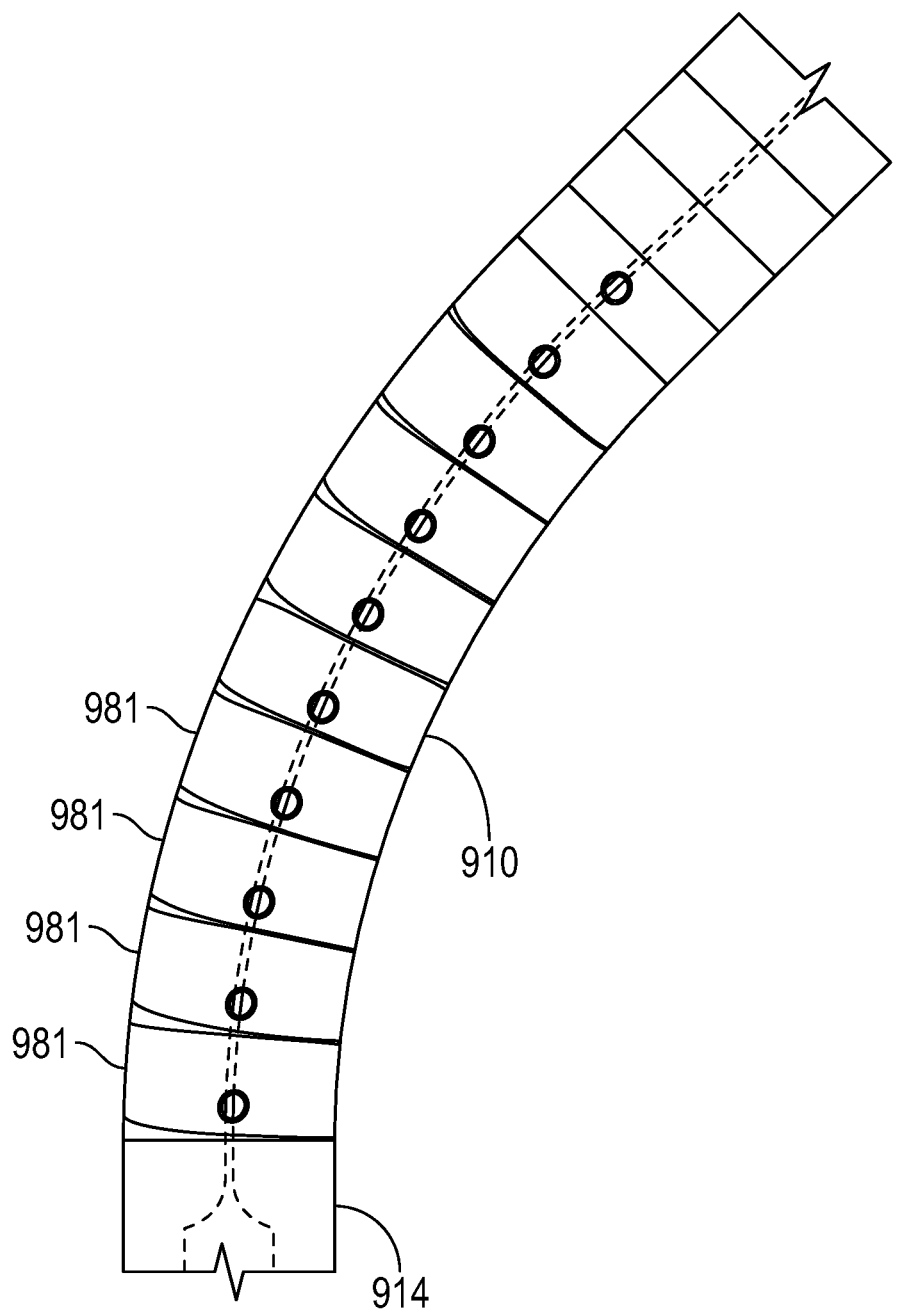
FIG. 9 is a side view of another articulating portion configured for use with the elongated body of the surgical instrument of FIG. 1 or 2 having a plurality of flexing sections.

Referring particularly to FIGS. 6A, 6B and 9, articulating portions 630, 910 of elongated bodies 614, 914 may include a plurality of flexing sections 681, 981 to control a degree of articulation of articulating portions 630, 910. The flexing sections 681, 981 allowing a gentle bend to be achieved by only allowing a certain amount of flex per section. As an example, each flexing sections 681, 981 may allow about 5 degrees of flex, thus using 9 flexing sections 681, 981 allows about 45 degrees total of bend. The flexing sections 681, 981 may only allow bend in one plane, by means of a pinned joint or hinge or partial cuts, or may be configured to bend in multiple planes.

Referring generally to FIGS. 2 and 4A, 4B, 5A, and 5B again, the surgical instrument 20 includes a housing 212 having the elongated body 214 extending distally therefrom. The elongated body 214 defines the first articulating portion 210 and the second articulating portion 230 distal of the first articulating portion 210. The elongated body 214 defines lumen 215 therein. End effector 200 is supported at distal end portion 218 of the elongated body 214. Ultrasonic transducer and generator assembly 220 is supported on the housing 212. Flexible waveguide 401 extends within the lumen 215 of the elongated body 214. Proximal end portion 480 of the flexible waveguide 401 is connected with the ultrasonic generator 220. Distal end portion 490 of the flexible waveguide 401 is connected with (attached to, integrally formed with, etc.) the blade 202 of the end effector 200. The flexible waveguide 401 defines first articulating portion 410 having a narrower dimension, e.g., width, than a width of other portions of the flexible waveguide 401. The flexible waveguide 401 defines second articulating portion 430 configured to articulate in a different direction (e.g., about the Z-axis direction of FIG. 4B) from the articulating direction of the first articulating portion 410 (e.g., about the Y-axis direction of FIG. 4A). Second articulating portion 430 has a different narrower dimension (as compared to first articulating portion 410), e.g., a narrowed height, than a height of other portions of the flexible waveguide 401.

The end effector 200 includes ultrasonic blade 202, which may be cylindrical or otherwise define one or more radial symmetries, and jaw 201, which may be configured to rotate about the ultrasonic blade 202. The ultrasonic blade 202 and the jaw 201 are configured to capture and treat tissue therebetween in a clamping position of jaw 201. Alternatively or additionally, ultrasonic blade 202 may be utilized to treat unclamped tissue in close proximity therewith. The elongated body 214 is configured to rotate (see, e.g., elongated body 614 of FIGS. 6A and 6B) to achieve different directional orientations of end effector 200.

The first rotation knob 222 is configured to rotate the elongated body 214 (e.g., to rotate the portion of the elongated body 214 proximal to the first articulating portion 210). The second rotation knob 223 is configured to rotate the jaw 201 about the ultrasonic blade 202, in embodiments where such rotation is provided. The third rotation knob 227 is configured to articulate the first articulating portion 210 of the elongated body 214 and, thus, the first articulating portion of the waveguide 410. The fourth rotation knob 228 is configured to articulate the second articulating portion 230 of the elongated body 214 and, thus, the second articulating portion 430 of the flexible waveguide.

Figure 10:
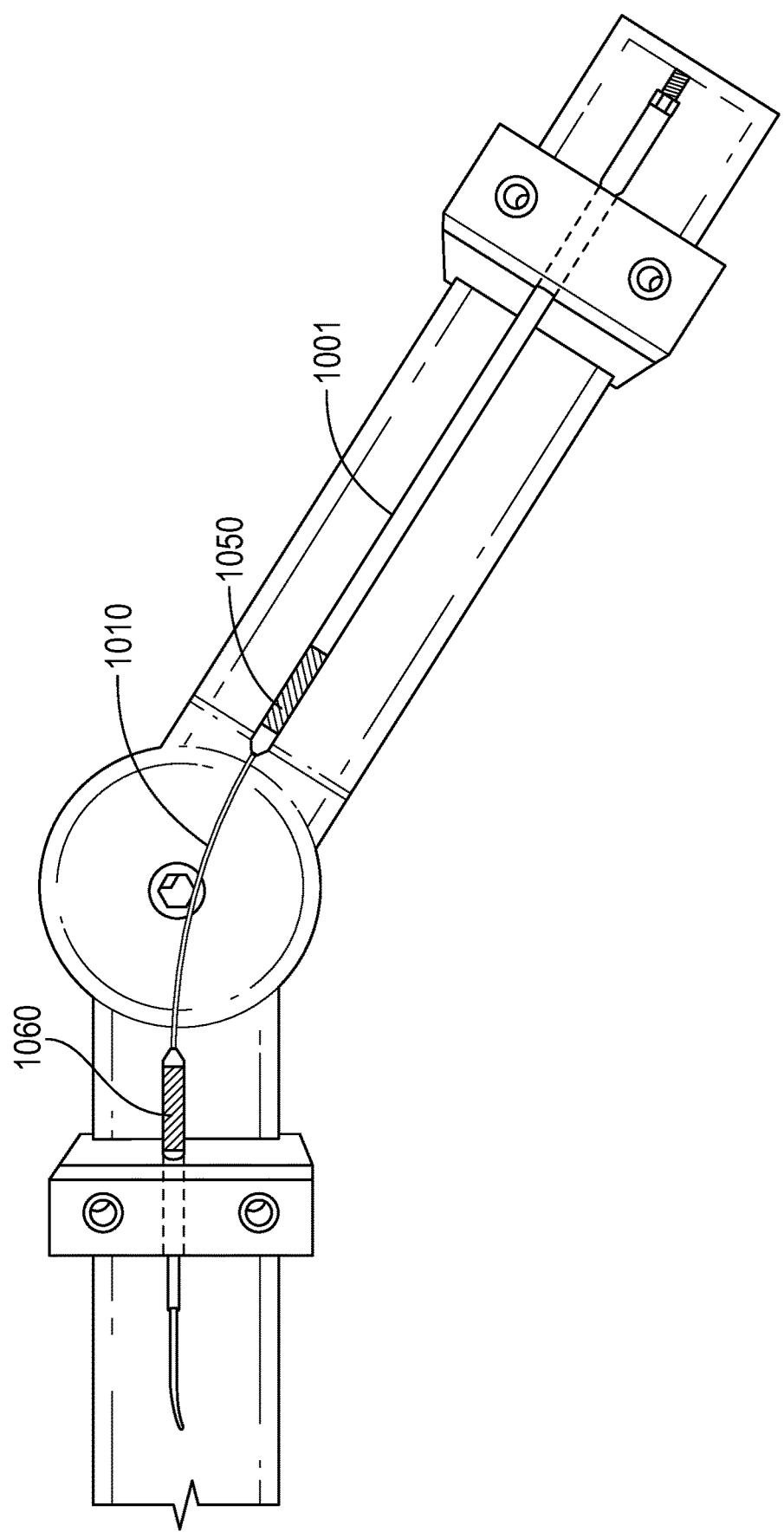
FIG. 10 is a side view of a conceptualized articulation portion including a flexible waveguide shown restrained in a test fixture representing support, pivot, and other features, the flexible waveguide configured for use with the surgical instrument of FIG. 1 or 2 and including transducers positioned at opposite sides of the articulating portion of the flexible waveguide.

Referring to FIG. 10, a first transducer 1050 and a second transducer 1060 are positioned at opposite sides, e.g., proximally and distally, of an articulating portion 1010 of a flexible waveguide 1001. The first and second transducers 1050 and 1060 amplify an ultrasonic wave transmitted through the articulating portion 1010 of the flexible waveguide 1001, e.g., the portion having the narrower width than the width of other portions of the flexible waveguide 1001. For example, the second transducer 1060 distal of the articulating portion 1010 amplifies the ultrasonic energy as the wave continues down the waveguide (i.e., makes up for any loss in energy resulting from the articulating portion 1010). In embodiments, only the transducer distal of articulation portion 1010, e.g., second transducer 1060, is provided. Similar transducers may be positioned at opposite sides (or only on the distal side) of each articulating portion of a flexible waveguide having multiple articulating portions along a length thereof.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 11:
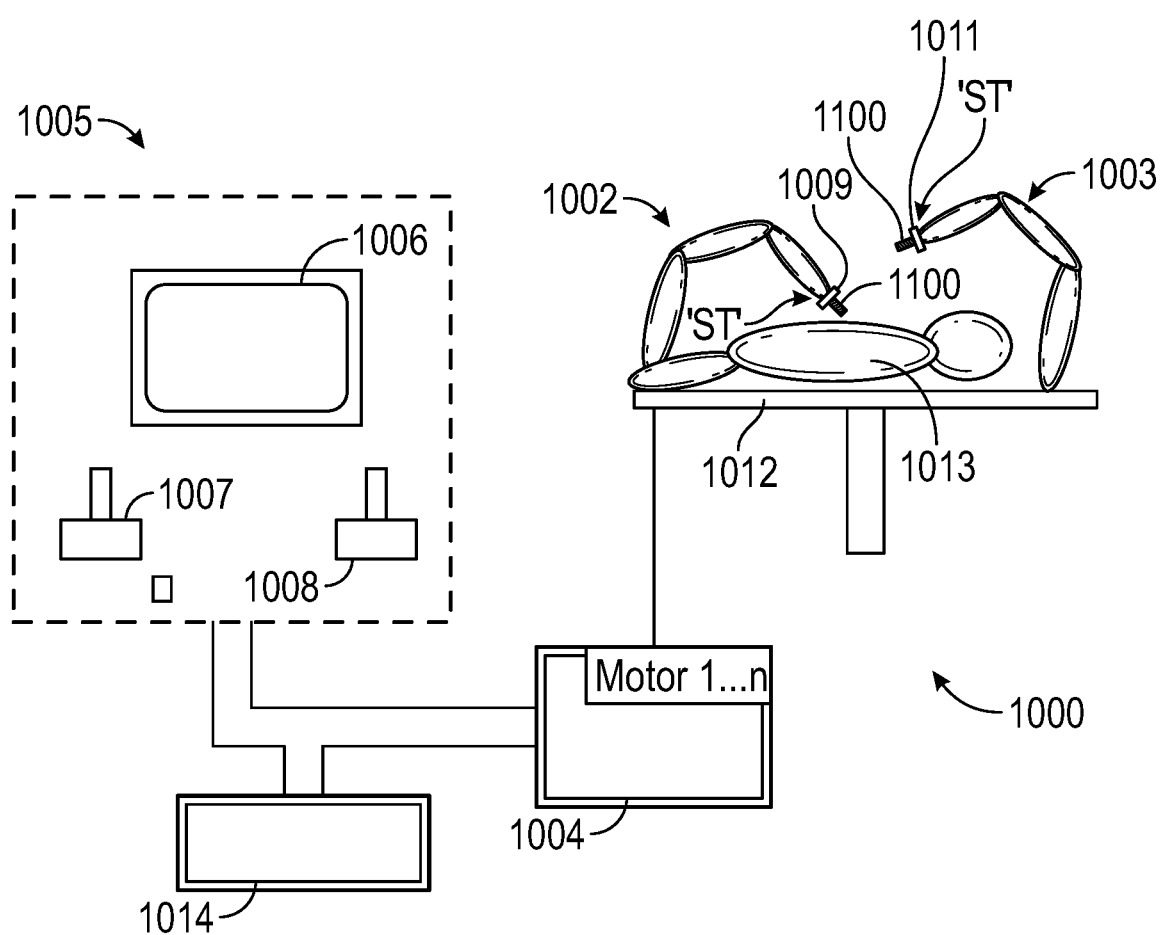
FIG. 11 is a schematic illustration of a robotic surgical system configured for use in accordance with the present disclosure.
Figure 12A:
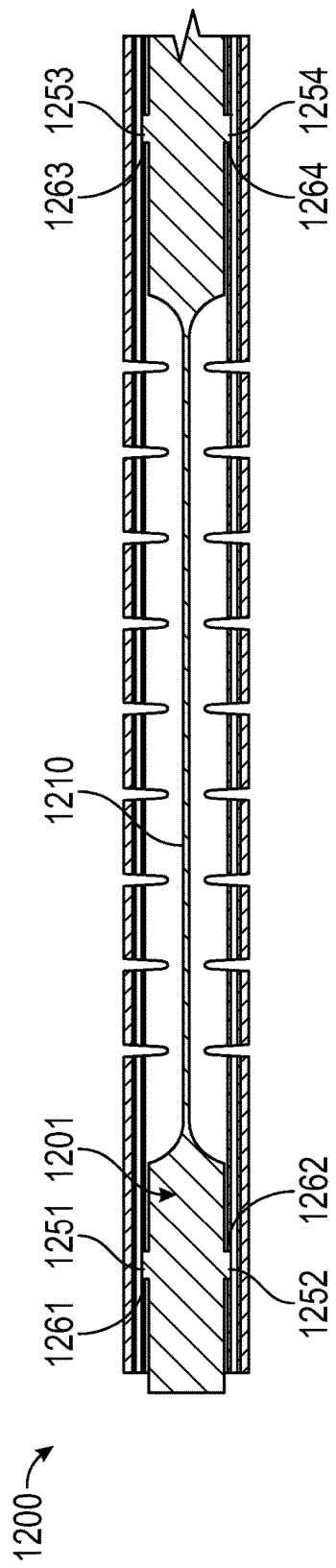
FIG. 12A is a longitudinal, cross-sectional view of a flexible waveguide secured within a lumen of an elongated body by a post and hole attachment structure.
Figure 12B:
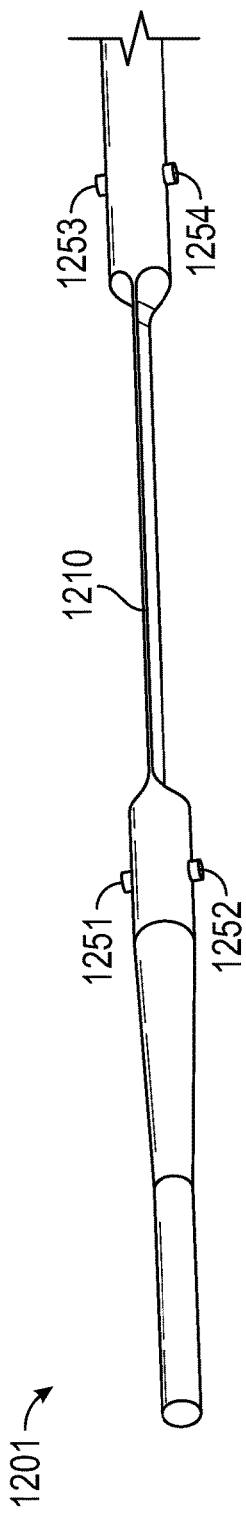
FIG. 12B is a perspective view of the flexible waveguide of FIG. 12A.
Figure 12C:
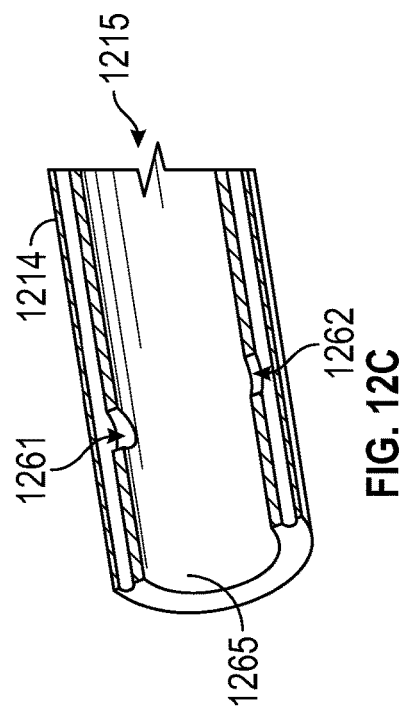
FIG. 12C is a longitudinal, cross-sectional view of the holes formed in an inner surface of the elongated body of FIG. 12A.
Figure 12D:
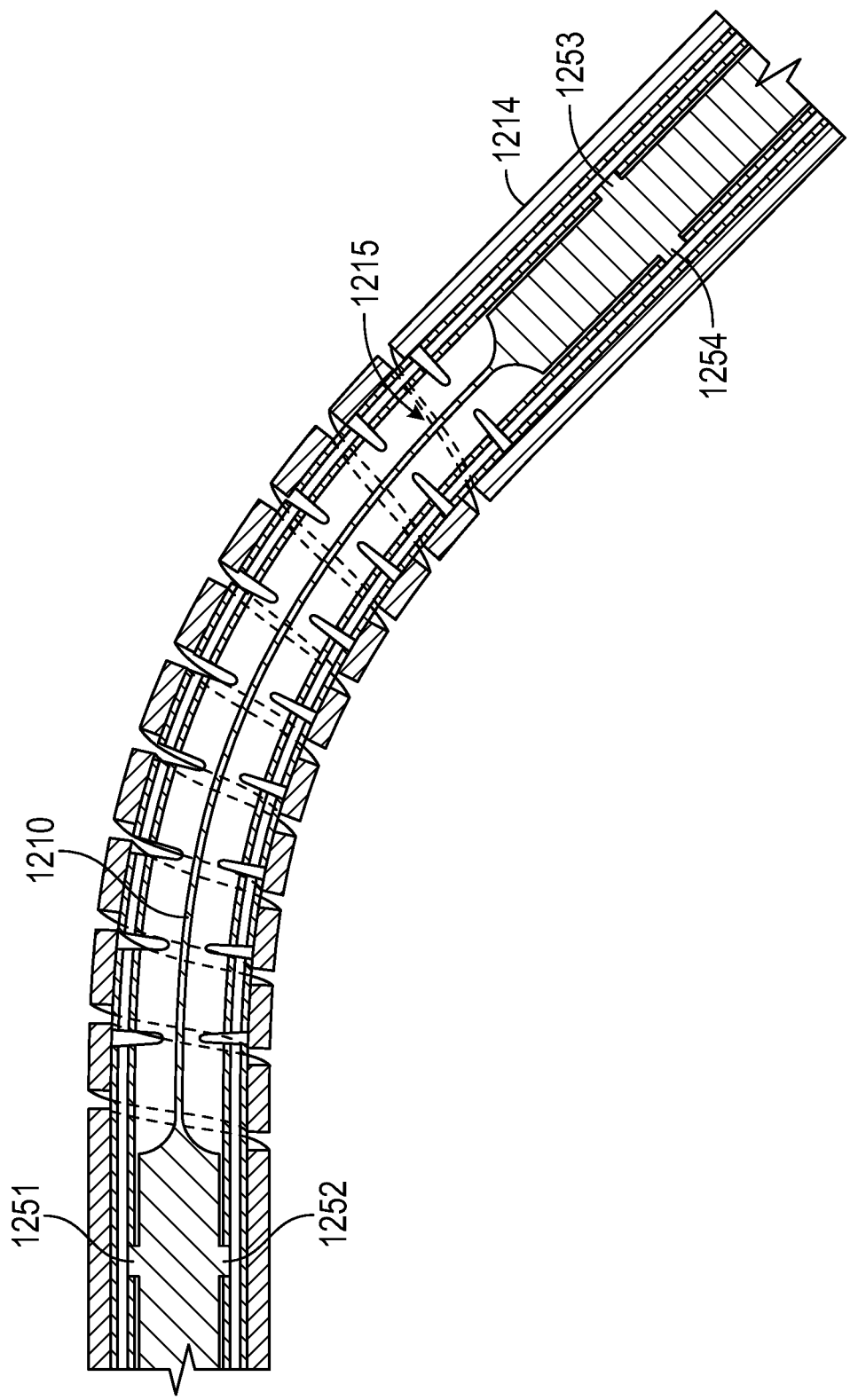
FIG. 12D is a longitudinal, cross-sectional view of the elongated body and the flexible waveguide of FIG. 12A in an articulated configuration.

FIG. 11 illustrates a medical work station shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below. In embodiments, end effector 1100 may include, for example the elongated body (or portion thereof) and end effector of any of the embodiments detailed therein; thus, robot arm 1003 (together with relevant portions of control device 1004, operating console 1005, and/or manual input devices 1007, 1008) functions are the housings 12, 212 (FIGS. 1 and 2, respectively) of the ultrasonic surgical instrument.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

Referring particularly to FIGS. 12A to 12D, a support system 1200 for flexible waveguide 1201 is described. The flexible waveguide 1201 includes a plurality of protruding posts 1251, 1252, 1253, 1254 extending from the flexible waveguide 1201. The protruding posts 1251 and 1252 are shaped and dimensioned to be received in corresponding recesses 1261 and 1262, respectively. Protruding posts 1253 and 1254 are similarly received in corresponding recesses 1263 and 1264, respectively. The recesses 1261 and 1262 are formed in an inner surface 1265 of elongated member 1214 and are configured to receive the protruding posts 1253 and 1254, respectively, therein to secure the flexible waveguide 1201 within lumen 1215 of elongated member 1214. Some of the plurality of protruding posts 1251, 1252, 1253, 1254 are positioned proximally of articulating portion 1210 and others of the plurality of protruding posts 1251, 1252, 1253, 1254 are positioned distally of articulating portion 1210 to allow articulation of the articulating portion 1210 within lumen 1215 and to prevent contact between articulating portion 1210 and the inner surface 1265 of elongated member 1214 (see, e.g., FIG. 12D).

Figure 13A:
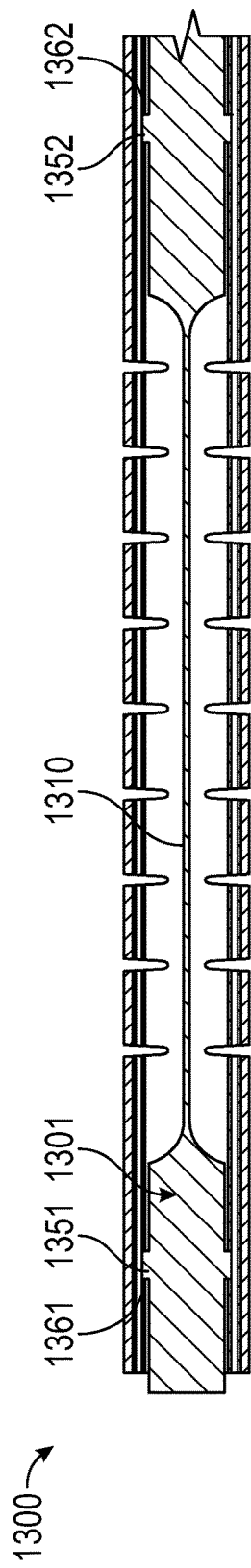
FIG. 13A is a longitudinal, cross-sectional view of a flexible waveguide secured within a lumen of an elongated body by an annular collar protruding outwardly from the flexible waveguide.
Figure 13B:
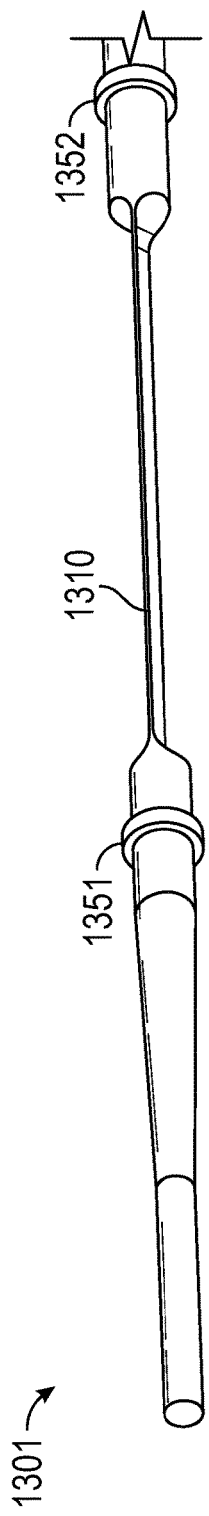
FIG. 13B is a perspective view of the flexible waveguide of FIG. 13A.
Figure 13C:
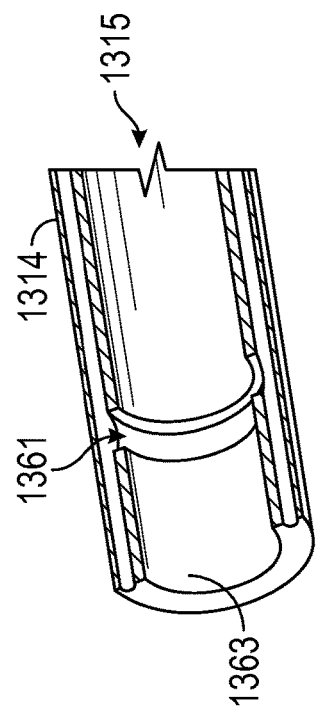
FIG. 13C is a longitudinal, cross-sectional view of a recess formed in an inner surface of the elongated body and configured to receive the annular collar of FIG. 13A.

Referring particularly to FIGS. 13A to 13C, a support system 1300 for flexible waveguide 1301 is described. The flexible waveguide 1301 includes a first annular collar 1351 and a second annular collar 1352 circumferentially protruding from the flexible waveguide 1301. first and second annular collars 1351 and 1352 are shaped and dimensioned to be received in a corresponding recess 1361, 1362, respectively. The recesses 1361 and 1362 are circumferentially formed in an inner surface 1363 of elongated member 1314 and are configured to receive the annular collars 1351 and 1352, respectively, therein to secure the flexible waveguide 1301 within lumen 1315 of elongated member 1314. The annular collars 1351, 1352 and recesses 1361, 1362 are positioned proximally and distally, respectively, of articulating portion 1310 to allow articulation of the articulating portion 1310 within lumen 1315 and to prevent contact between articulating portion 1310 and the inner surface 1363 of elongated member 1314.

Figure 14A:
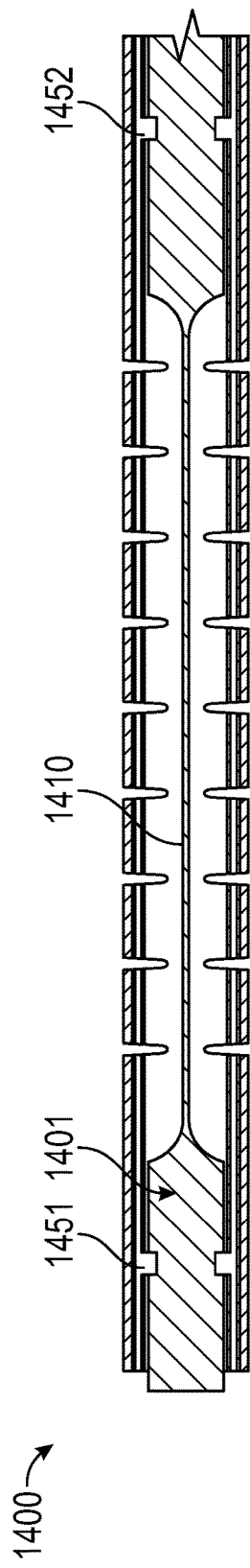
FIG. 14A is a longitudinal, cross-sectional view of a flexible waveguide secured within a lumen of an elongated body by an annular collar protruding inwardly from an inner surface of the elongated body.
Figure 14B:
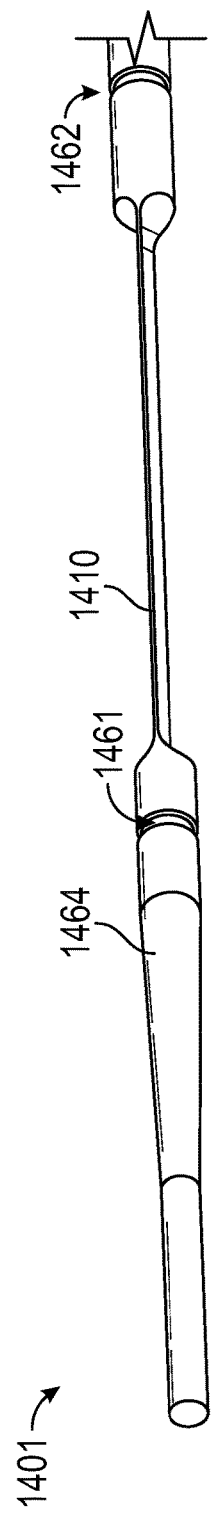
FIG. 14B is a perspective view of the flexible waveguide including a recess configured to receive the annular collar of FIG. 14A.
Figure 14C:
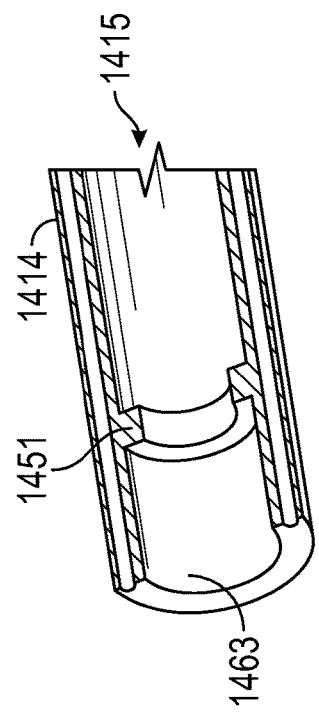
FIG. 14C is a longitudinal, cross-sectional view of the annular collar protruding from the inner surface of the elongated body of FIG. 14A.

Referring particularly to FIGS. 14A to 14C, a support system 1400 for flexible waveguide 1401 is described. The flexible waveguide 1401 includes a first recess 1461 and a second recess 1462 circumferentially formed in an outer surface 1464 of the flexible waveguide 1401. The first and second recesses 1461 and 1462 are shaped and dimensioned to receive annular collars 1451 and 1452, respectively. The annular collars 1451 and 1452 protrude circumferentially from an inner surface 1463 of elongated member 1414 and are configured to be received in the first and second recesses 1461 and 1462, respectively, to secure the flexible waveguide 1401 within lumen 1415 of elongated member 1414. The annular collars 1451, 1452 and recesses 1461, 1462 are positioned proximally and distally, respectively, of articulating portion 1410 to allow articulation of the articulating portion 1410 within lumen 1415 and to prevent contact between articulating portion 1410 and the inner surface 1463 of elongated member 1414.

Referring particularly to FIGS. 15A to 15D, a support system 1500 for flexible waveguide 1501 is described. Removable annular collars 1551 and 1552 are positioned about flexible waveguide 1501. The removable annular collars 1551 and 1552 may each be formed of or include plastic or silicone. The removable annular collars 1551 and 1552 may allow some degree of longitudinal movement within lumen 1515 of elongated member 1514 to prevent stress to the flexible waveguide 1501. The removable annular collars 1551 and 1552 are positioned proximally and distally, respectively, of articulating portion 1510 to allow articulation of the articulating portion 1510 within lumen 1515 and to prevent contact between articulating portion 1510 and the inner surface 1563 of elongated member 1514.

The lumen 1515 may include a first recess 1561 and a second recess 1562 circumferentially formed in the inner surface 1563 of the lumen 1515. The first and second recesses 1561 and 1562 are shaped and dimensioned to receive removable annular collars 1551 and 1552, respectively.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a housing having an elongated body extending distally therefrom, the elongated body defining a first articulating portion and a second articulating portion, and the elongated body defining a lumen therein;
    an end effector supported at a distal end portion of the elongated body;
    a flexible waveguide extending through the lumen of the elongated body, a distal end portion of the flexible waveguide configured to connect with the end effector, the flexible waveguide defining a first articulating portion having a narrower thickness than a thickness of other portions of the flexible waveguide; and
    first and second transducers disposed on opposite sides of the first articulating portion of the flexible waveguide, at least one of the first or second transducers configured to amplify an ultrasonic wave transmitted through the first articulating portion of the flexible waveguide.

2. The surgical instrument of claim 1, wherein the first articulating portion of the flexible waveguide is configured to articulate in a first orientation, and wherein a second articulating portion of the flexible waveguide is configured to articulate in a second orientation.

3. The surgical instrument of claim 1, wherein the first articulating portion of the flexible waveguide and a second articulating portion of the flexible waveguide are configured to articulate in a same orientation as each other.

4. The surgical instrument of claim 1, wherein the end effector includes an ultrasonic blade and a jaw configured to rotate about the ultrasonic blade, the ultrasonic blade and the jaw configured to capture and treat tissue therebetween in plural rotational orientations of the jaw relative to the ultrasonic blade.

5. The surgical instrument of claim 4, wherein the elongated body is configured to rotate to achieve different directional orientations of the end effector.

6. The surgical instrument of claim 5, wherein independent controls are configured to: rotate the elongated body; rotate the jaw about the ultrasonic blade; and articulate the first articulating portion of the elongated body and, thus, the first articulating portion of the flexible waveguide.

7. A surgical instrument, comprising:
a housing having an elongated body extending distally therefrom, the elongated body defining a first articulating portion, and the elongated body defining a lumen therein;
an end effector supported at a distal end portion of the elongated body; and
a flexible waveguide extending through the lumen of the elongated body, a proximal end portion of the flexible waveguide configured to connect to an ultrasonic transducer, and a distal end portion of the flexible waveguide configured to connect with the end effector,
the flexible waveguide defining a first articulating portion extending through the first articulating portion of the elongated body and having a first dimension narrower than a first dimension of other portions of the flexible waveguide,
wherein the elongated body and the flexible waveguide are longitudinally fixed and rotatably coupled by a proximal annular collar and annular slot engagement proximally of the first articulating portions of the elongated body and the flexible waveguide and longitudinally fixed and rotatably coupled by a distal annular collar and annular slot engagement distally of the first articulating portions of the elongated body and the flexible waveguide.

8. The surgical instrument of claim 7, wherein the first articulating portion of the flexible waveguide is configured to articulate in a first orientation, and wherein a second articulating portion of the flexible waveguide is configured to articulate in a second orientation.

9. The surgical instrument of claim 8, wherein each of the first and second articulating portions of the flexible waveguide is configured to articulate from about 1 degree to about 45 degrees.

10. The surgical instrument of claim 7, wherein the end effector includes an ultrasonic blade and a jaw configured to rotate about the ultrasonic blade, the ultrasonic blade and the jaw configured to capture and treat tissue therebetween in plural rotational orientations of the jaw relative to the ultrasonic blade.

11. The surgical instrument of claim 10, wherein the elongated body is configured to rotate relative to the flexible waveguide.

12. The surgical instrument of claim 11, wherein independent controls are configured to: rotate the elongated body; rotate the jaw about the ultrasonic blade; and articulate the first articulating portion of the elongated body and, thus, the first articulating portion of the flexible waveguide.

13. The surgical instrument of claim 7, further including first and second transducers at opposite sides of the first articulating portion of the flexible waveguide, at least one of the first or second transducers configured to amplify an ultrasonic wave transmitted through the first articulating portion of the flexible waveguide.

14. An end effector of a surgical instrument, comprising:
an elongated body defining a first joint configured to pivot about a first axis in a first dimension substantially perpendicular to the first axis and a second joint configured to pivot about a second axis in a second dimension substantially perpendicular to the second axis, the elongated body defining a lumen therein, and the elongated body supporting an end effector at a distal end portion thereof; and
a flexible waveguide extending through the lumen,
the flexible waveguide defining a first articulating portion extending through the first joint and having a width in the first dimension narrower than a width in the first dimension of other portions of the flexible waveguide to facilitate pivoting of the first articulating portion in the first dimension, and the flexible waveguide defining a second articulating portion extending through the second joint and having a width in the second dimension narrower than a width in the second dimension of other portions of the flexible waveguide to facilitate pivoting of the second articulating portion in the second dimension.

15. The end effector of claim 14, wherein each of the first and second articulating portions of the flexible waveguide is configured to articulate from about 1 degree to about 45 degrees.

16. The end effector of claim 14, wherein the end effector includes an ultrasonic blade and a jaw configured to rotate about the ultrasonic blade, the ultrasonic blade and the jaw configured to capture and treat tissue therebetween in plural rotational orientations of the jaw relative to the ultrasonic blade.

17. The end effector of claim 16, wherein the elongated body is configured to rotate.

18. The end effector of claim 14, further including first and second transducers at opposite sides of the first articulating portion of the flexible waveguide, the first or second transducers configured to amplify an ultrasonic wave transmitted through the first articulating portion of the flexible waveguide.

19. A robotic surgical system, comprising:
a control device and a robotic arm;
an elongated body defining a first articulating portion and, the elongated body defining a lumen therein, and the elongated body supporting an end effector at a distal end portion thereof, wherein the robotic arm is configured to control the elongated body and the end effector;
a flexible waveguide extending through the lumen, the flexible waveguide defining a first articulating portion having a narrower thickness than a thickness of other portions of the flexible waveguide; and
first and second transducers disposed on opposite sides of the first articulating portion of the flexible waveguide, at least one of the first or second transducers configured to amplify an ultrasonic wave transmitted through the first articulating portion of the flexible waveguide.

20. The robotic surgical system of claim 19, wherein the first articulating portion of the flexible waveguide is configured to articulate in a first orientation, and wherein a second articulating portion of the flexible waveguide is configured to articulate in a second orientation.

21. The robotic surgical system of claim 20, wherein the first orientation is different from the second orientation.

22. A surgical instrument, comprising:
- a housing having an elongated body extending distally therefrom, the elongated body defining an articulating portion, and the elongated body defining a lumen therein;
- an end effector supported at a distal end portion of the elongated body;
- a flexible waveguide extending through the lumen of the elongated body, a proximal end portion of the flexible waveguide configured to connect to an ultrasonic transducer, and a distal end portion of the flexible waveguide configured to connected with the end effector, the flexible waveguide defining an articulating portion extending through the articulating portion of the elongated body and having a narrower width than a width of other portions of the flexible waveguide;
- a distal stabilizer securing the flexible waveguide to the elongated body at a position distal of the articulating portion of the elongated body and the articulating portion of the flexible waveguide; and
- a first articulation cable extending from the housing through the articulating portion of the elongated body to engage the distal stabilizer, wherein manipulation of the first articulation cable articulates the articulating portions of the elongated body and the flexible waveguide.

23. The surgical instrument of claim 22, wherein the elongated body is configured to rotate to achieve different directional orientations of the end effector.

24. The surgical instrument of claim 22, further comprising a second articulation cable extending from the housing through the articulating portion of the elongated body to engage the distal stabilizer, wherein manipulation of the second articulation cable articulates the articulating portions of the elongated body and the flexible waveguide in a direction different from a direction of articulation in response to manipulation of the first articulation cable.

25. The surgical instrument of claim 22, wherein the first articulation cable extends along the flexible waveguide within the elongated body.

* * * * *